(12) United States Patent
Ueda

(10) Patent No.: US 8,483,811 B2
(45) Date of Patent: Jul. 9, 2013

(54) DETECTION OF BIOLOGICAL INFORMATION OF A SUBJECT

(75) Inventor: Tomoaki Ueda, Kyoto (JP)

(73) Assignee: Empire Technology Development LLC, Wilmington, DE (US)

( * ) Notice: Subject to any disclaimer, the term of this patent is extended or adjusted under 35 U.S.C. 154(b) by 165 days.

(21) Appl. No.: 13/000,127

(22) PCT Filed: Aug. 2, 2010

(86) PCT No.: PCT/JP2010/004869
§ 371 (c)(1),
(2), (4) Date: Jan. 18, 2011

(87) PCT Pub. No.: WO2012/017473
PCT Pub. Date: Feb. 9, 2012

(65) Prior Publication Data
US 2012/0053480 A1    Mar. 1, 2012

(51) Int. Cl.
*A61B 5/04* (2006.01)
(52) U.S. Cl.
USPC .............................. 600/513; 600/508
(58) Field of Classification Search
USPC ................... 600/508–509, 513, 516
See application file for complete search history.

(56) References Cited

U.S. PATENT DOCUMENTS

| 5,211,178 | A | 5/1993 | Kado et al. |
| 7,166,201 | B2 | 1/2007 | Wolf |
| 7,238,267 | B2 | 7/2007 | Wolf et al. |
| 2006/0058694 | A1 | 3/2006 | Clark et al. |
| 2006/0235315 | A1* | 10/2006 | Akselrod et al. ............... 600/509 |
| 2007/0255152 | A1* | 11/2007 | Park et al. ...................... 600/513 |
| 2007/0282212 | A1* | 12/2007 | Sierra et al. ................... 600/529 |

FOREIGN PATENT DOCUMENTS

| JP | 04-141140 | 5/1992 |
| JP | 2003-175009 | 6/2003 |
| JP | 2005-511174 | 4/2005 |
| JP | 2007-512876 | 5/2007 |
| JP | 2010-000315 | 1/2010 |
| JP | 2010-051387 | 3/2010 |
| WO | WO 03/048789 | 6/2003 |
| WO | WO 2005/053542 | 6/2005 |

OTHER PUBLICATIONS

International Search Report and Written Opinion for International Patent Application No. PCT/JP2010/004869 mailed on Nov. 2, 2010.
"Obstructive sleep apnea—Dental Devices," Accessed at http://www.umm.edu/patiented/articles/what_dental_devices_used_treat_sleep_apnea_000065_9.htm, accessed on May 30, 2012, pp. 3.
Optimum Bedside Cardiac Monitoring (Jacobson C. Progress in Cardiovascular Nursing (2000) 134-137.

(Continued)

*Primary Examiner* — Rex R Holmes
(74) *Attorney, Agent, or Firm* — IPUSA, PLLC

(57) ABSTRACT

Implementations and techniques for detecting biological information of a subject based on one of a rectangular wave to rectangular wave (RR) interval in an electrocardiogram and/or a change in impedance of a human body when alternating current modulated by a code sequence having an autocorrelation property is applied to the human body are generally disclosed.

2 Claims, 17 Drawing Sheets

OTHER PUBLICATIONS

Optimization of Electrode Positions of a Wearable ECG Monitoring System for . . . Jiang Y et al. Computers in Cardiology (2009)36:293-296).

Cervical Positioning for Reduction of Sleep-Disordered Breathing in Mild-to-Moderate OSAS (Kushida CA et al. Sleep Breathing (2001)5(2):71-78).

Bariatric Surgery (Buchwald H et al. JAMA (2004)294(12):1724-1737.

Clinical Guidelines for the Use of Unattended Portable Monitors in the Diagnosis of . . . Collop Na et al. JCSM Journal of Clinical Sleep Medicine, vol. 3, No. 7, 2007, 737-747.

Portable Obstructive Sleep Apnea Screening System Using Overnight ECG and a PDA-based wireless Transmission system (Chang KM. Telemed e-Health (2009)15(4): 353-361).

http://www.cigna.com/healthinfo/hw49127.html, Jan. 20, 2012.

* cited by examiner

Fig. 16

| INPUT | | 3-VALUE LOGIC | OUTPUT |
|---|---|---|---|
| 1 | 1 | POSITIVE PULSE | 1 |
| 1 | 0 | 0 LEVEL | 0 |
| 0 | 1 | 0 LEVEL | 0 |
| 0 | 0 | NEGATIVE PULSE | 1 | though the subject sleeps. The non-contact electrocardiograph 110 may be configured by using techniques disclosed in WO2003/048789, the entire contents of which are hereby incorporated by reference. As shown in the illustrated example, the non-contact electrocardiograph 110 may include two electrodes 111, 112 and an amplifier 113. The electrodes 111, 112 may be provided on a pad in such a manner that they may be in indirect contact with left and right shoulders, respectively, of the back of the subject when the subject sleeps on the pad on his or her back. The electrodes 111, 112 may be buried in the pad or be attached to the pad, for example. In an example, the pad may be provided on a bed. The amplifier 113 may be configured to operate on the current input from the electrodes 111, 112 as input bias current. In some examples, the amplifier 113 may be an amplifier with an extremely high impedance operating on fA (femtoampere)-class input bias current. In some examples, the amplifier 113 may include filters such as a lowpass filter.

DETECTION OF BIOLOGICAL INFORMATION OF A SUBJECT

RELATED APPLICATION

This is the National Stage Entry of PCT Application Number PCT/JP2010/004869 filed Aug. 2, 2010.

BACKGROUND

Unless otherwise indicated herein, the approaches described in this section are not prior art to the claims in this application and are not admitted to be prior art by inclusion in this section.

Biological information of a subject (i.e., a patient) is useful for detecting a health condition of the subject.

Therefore, it is desired to provide useful ways of detecting biological information of a subject.

SUMMARY

According to an embodiment, an apparatus is provided which is configured detect a respiration condition of a subject based on a rectangular wave to rectangular wave (RR) interval in an electrocardiogram.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 16 is a table illustrating an operation of a 3-value logic detection circuit 1520.

DETAILED DESCRIPTION

Figure 1:
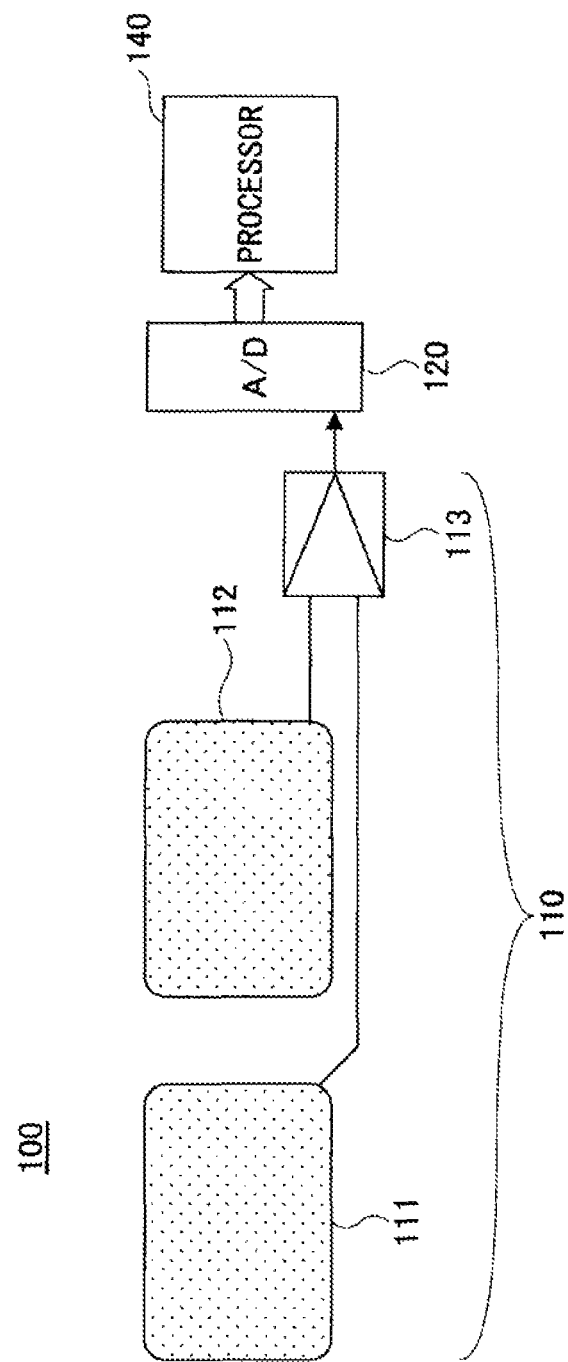
FIG. 1 is a diagram illustrating an embodiment of an apparatus 100 for detecting a respiration condition of a subject.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

FIG. 1 shows an embodiment of an apparatus 100 for detecting a respiration condition of a subject.

As illustrated, the apparatus 100 may include a non-contact electrocardiograph 110, an analog-to-digital converter 120, and a processor 140.

The non-contact electrocardiograph 110 may be configured to measure an electrocardiogram in a non-contact manner when the subject sleeps. The non-contact electrocardiograph 110 may be configured by using techniques disclosed in WO2003/048789, the entire contents of which are hereby incorporated by reference. As shown in the illustrated example, the non-contact electrocardiograph 110 may include two electrodes 111, 112 and an amplifier 113. The electrodes 111, 112 may be provided on a pad in such a manner that they may be in indirect contact with left and right shoulders, respectively, of the back of the subject when the subject sleeps on the pad on his or her back. The electrodes 111, 112 may be buried in the pad or be attached to the pad, for example. In an example, the pad may be provided on a bed. The amplifier 113 may be configured to operate on the current input from the electrodes 111, 112 as input bias current. In some examples, the amplifier 113 may be an amplifier with an extremely high impedance operating on fA (femtoampere)-class input bias current. In some examples, the amplifier 113 may include filters such as a lowpass filter.

The analog-to-digital converter 120 may be configured to digitize the electrocardiogram supplied from the non-contact electrocardiograph 110. The analog-to-digital converter 120 may be any type of analog-to-digital converter.

The processor 140 may be comprised of a microprocessor that may include a CPU, a ROM, a RAM, etc., which are interconnected via appropriate buses. The ROM may store the computer readable programs to be carried out by the CPU and data. The processor 140 may include or be connected to any other hardware resources such as an ASIC (Application Specific Integrated Circuit) in order to implement the functions described herein. Further, the analog-to-digital converter 120 may be incorporated in the processor 140.

Figure 2:
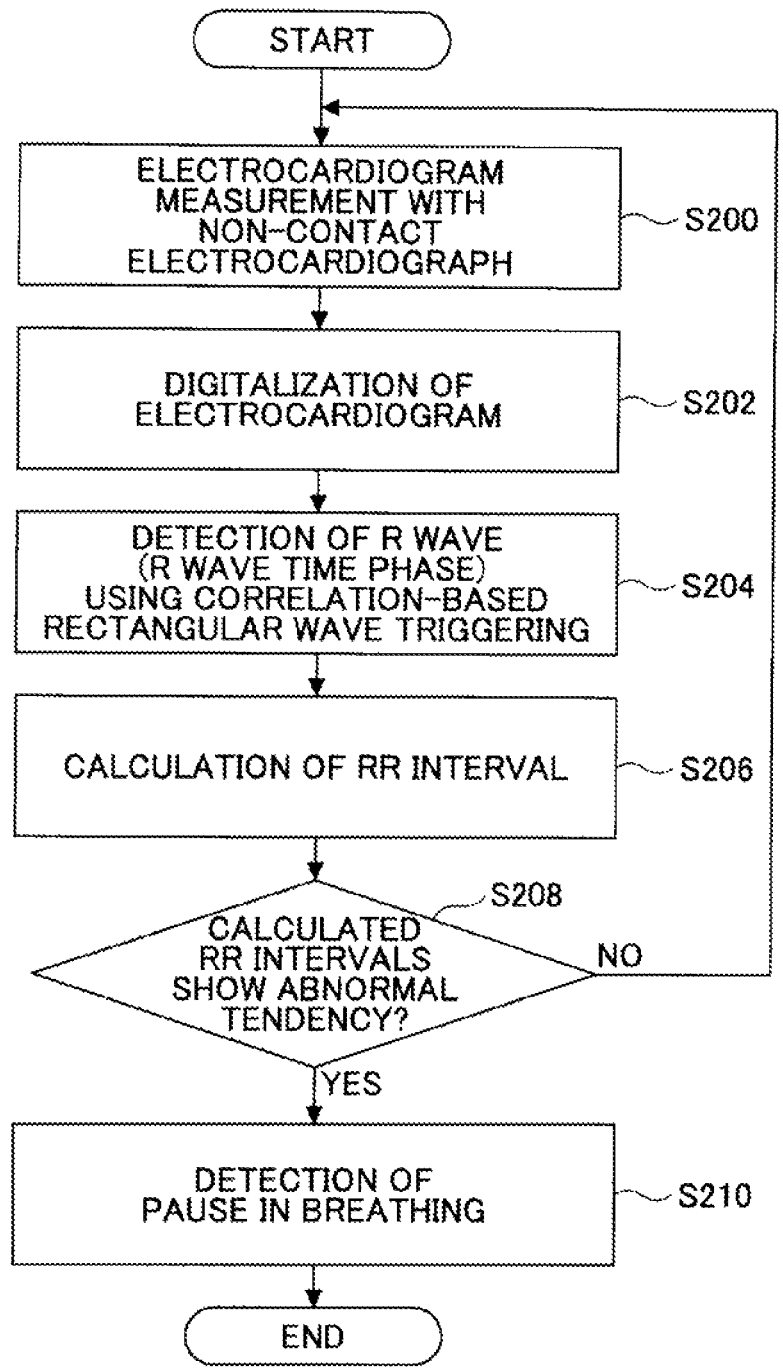
FIG. 2 is a flowchart illustrating an example of a method of detecting a respiration condition of a subject.

FIG. 2 shows an example of a method of detecting a respiration condition of a subject. The process routine shown in FIG. 2 may be initiated automatically when the subject lies down on the pad, and may be performed repeatedly while the subject sleeps on the pad. The subject on the pad may be detected by any method. For example, the subject on the pad may be detected by monitoring a pressure or load applied to the pad or a pillow.

In step 200, an electrocardiogram is measured with the non-contact electrocardiograph 110. In step 202, the measured electrocardiogram is digitized by the analog-to-digital converter 120. In some examples, the electrocardiogram measured with a non-contact electrocardiograph may be superimposed by commercial power noise (i.e., hum) of 50 Hz or 60 Hz. Such noise may be removed by a notch filter, a moving average filter, or any other suitable filter.

Figure 3:
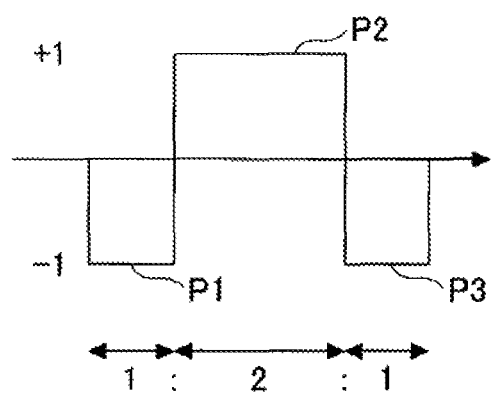
FIG. 3 is a diagram illustrating an example of a rectangular-wave time window.

In step 204, an R wave (rectangular wave) in the electrocardiogram (i.e., R wave time phase) may be detected by the processor 140. The R wave in the electrocardiogram may be detected by applying a correlation-based rectangular wave triggering method disclosed in JP04-141140, the entire contents of which are hereby incorporated by reference. For example, the R wave in the electrocardiogram may be detected by calculating a cross-correlation between the electrocardiogram and a rectangular-wave time window as shown in FIG. 3. The rectangular-wave time window may be constructed by a set that may include a first negative pulse P1, a positive pulse P2 and a second negative pulse P3 in this order, as shown in FIG. 3. In the example shown in FIG. 3, the ratio of widths of the first negative pulse P1, the positive pulse P2 and the second negative pulse P3 is about 1:2:1. This ratio may correspond to a ratio of ordinary widths of a Q wave, an R wave and an S wave. The rectangular-wave time window may have an amplitude of about plus or minus 1. A width of the rectangular-wave time window may be determined in such a manner that it may correspond to the width of a QRS complex (i.e., QRS width). In an example, an actual sampling rate of the non-contact electrocardiograph 110 may be between about 500 SPS (samples per second) and about 1 KSPS, and the width of the rectangular-wave time window may be on the order of about 60 to 80 ms, which may correspond to the width of the QRS complex. The R wave in the electrocardiogram may be detected at a point where the cross-correlation between the electrocardiogram and the rectangular-wave time window becomes a local maximum. In other words, the phase of the R wave in the electrocardiogram may be detected when the cross-correlation between the electrocardiogram and the rectangular-wave time window takes a correlation peak value.

Figure 4:
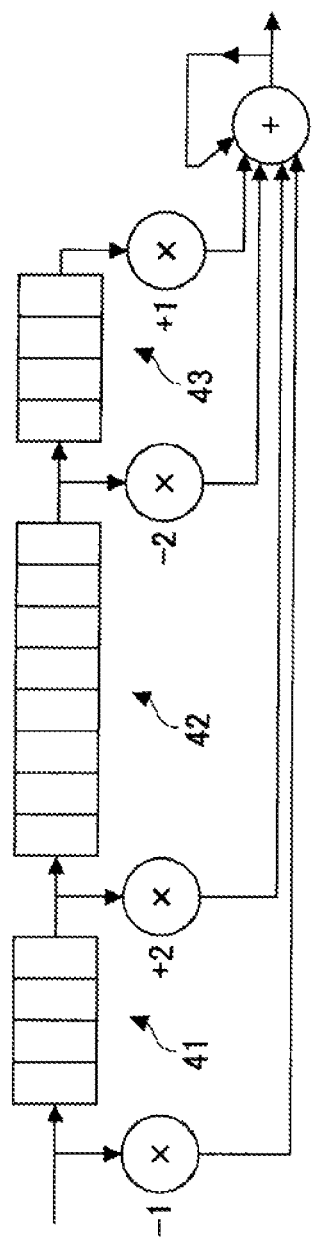
FIG. 4 is a diagram illustrating an example of a way of calculating cross-correlation between an electrocardiogram and a rectangular-wave time window.

In some examples, the cross-correlation between the electrocardiogram and the rectangular-wave time window may be calculated efficiently by calculating only differences, as schematically shown in FIG. 4. In the example shown in FIG. 4, a FIFO (first-in, first-out) data buffer (memory) having 16 areas may be used. In the first four areas 41, four discrete samples (the newest four samples) of the electrocardiogram may be stored. In the second eight areas 42, eight discrete samples (the second newest eight samples) of the electrocardiogram may be stored. In the third four areas 43, four discrete samples (the third newest four samples) of the electrocardiogram may be stored. For example, at a certain timing T1, a total of sixteen samples D1-D16 may be stored in the FIFO data buffer. Thus, the cross-correlation between the electrocardiogram and the rectangular-wave time window can be expressed by $$SUM(T1) = -D1-D2-D3-D4+D5+D6+D7+D8+D9+D10+D11+D12-D13-D14-D15-D16$$

At the next timing T2, a total of sixteen samples D0-D5 may be stored in the FIFO data buffer. In other words, samples D1-D15 may be shifted to the respective right areas while the oldest sample D16 may be output and a sample D0 may be newly input. At this timing, the cross-correlation between the electrocardiogram and the rectangular-wave time window can be expressed by $$SUM(T2) = -D0-D1-D2-D3+D4+D5+D6+D7+D8+D9+D10+D11-D12-D13-D14-D15$$

Here, the SUM(T2) can be calculated using the following relationship, $$SUM(T2) = SUM(T1) - D0 + 2D4 - 2D12 + D16$$

The configuration shown in FIG. 4 may be based on this relationship:

$$SUM(T2) = SUM(T1) - D0 + 2D4 - 2D12 + D16$$

Referring to FIG. 2 again, in step 206, an RR interval may be calculated by the processor 140. The RR interval may be a time interval between two consecutive R waves (i.e., a time interval between R wave time phases of the two consecutive R waves) detected in step 204 in time series. In this way, an RR interval may be calculated in real time by the processor 140.

In step 208, it may be determined by the processor 140 whether the calculated RR interval shows an abnormal tendency. Examples of this process are described later in detail. If it is determined that the calculated RR interval shows an abnormal tendency, the process routine may continue at step 210. On the other hand, if it is determined that the calculated RR interval does not show an abnormal tendency, the process routine may return to step 200, concluding that no pause in breathing is detected.

In step 210, it may be determined by the processor 140 that a pause in breathing is detected.

Figure 5:
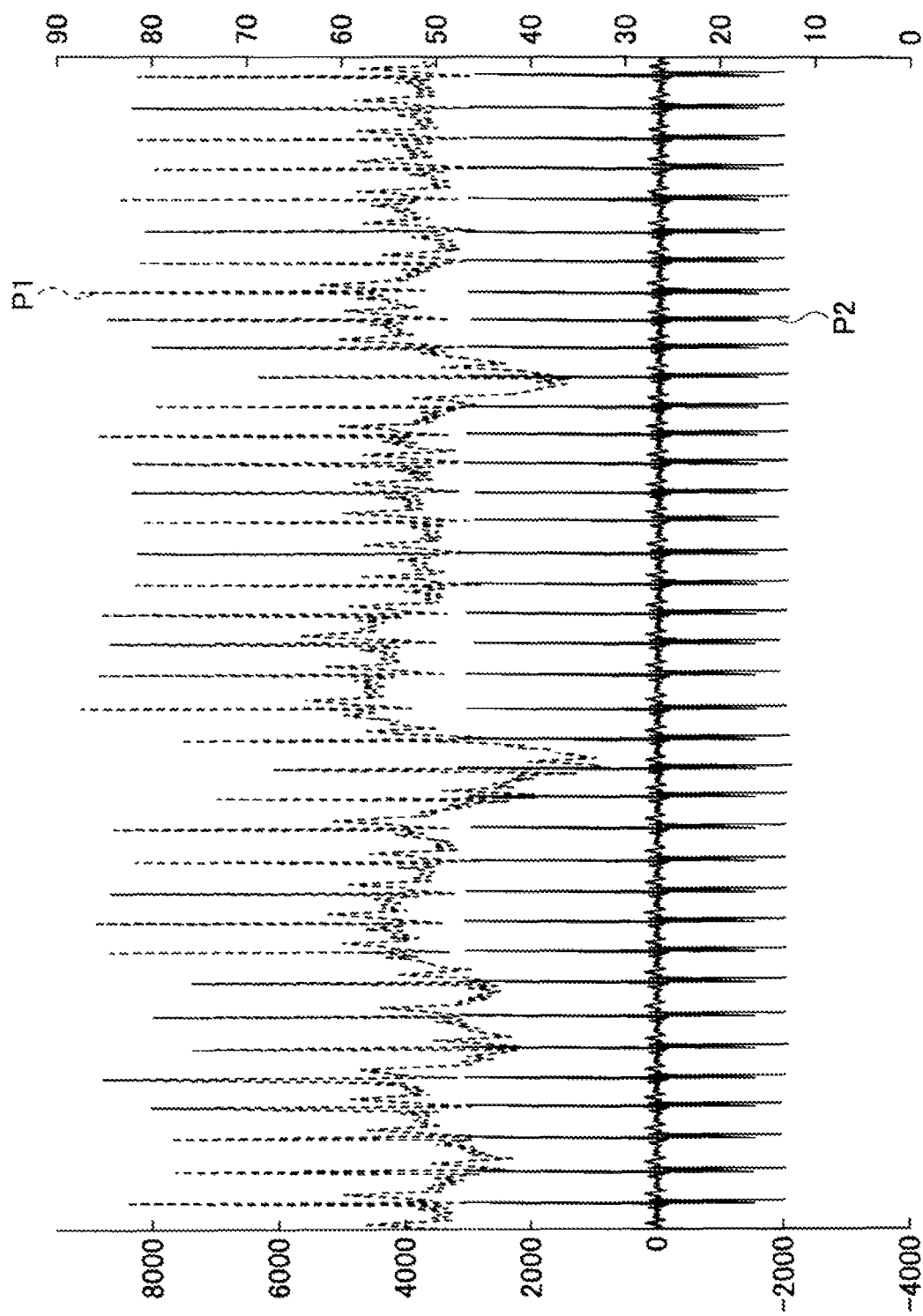
FIG. 5 is a diagram illustrating an example of time-series data of the electrocardiogram and the cross-correlation.

FIG. 5 shows an example of time-series data (waveforms) of the electrocardiogram and the cross-correlation. The electrocardiogram (the original waveform) example is indicated by reference symbol P1. The change in the correlation values, that is to say, the waveforms of the calculated cross-correlation between the electrocardiogram and the rectangular-wave time window is indicated by reference symbol P2. As shown in FIG. 5, R waves in the electrocardiogram can be detected based on the cross-correlation using the rectangular-wave time window described above.

Figure 6:
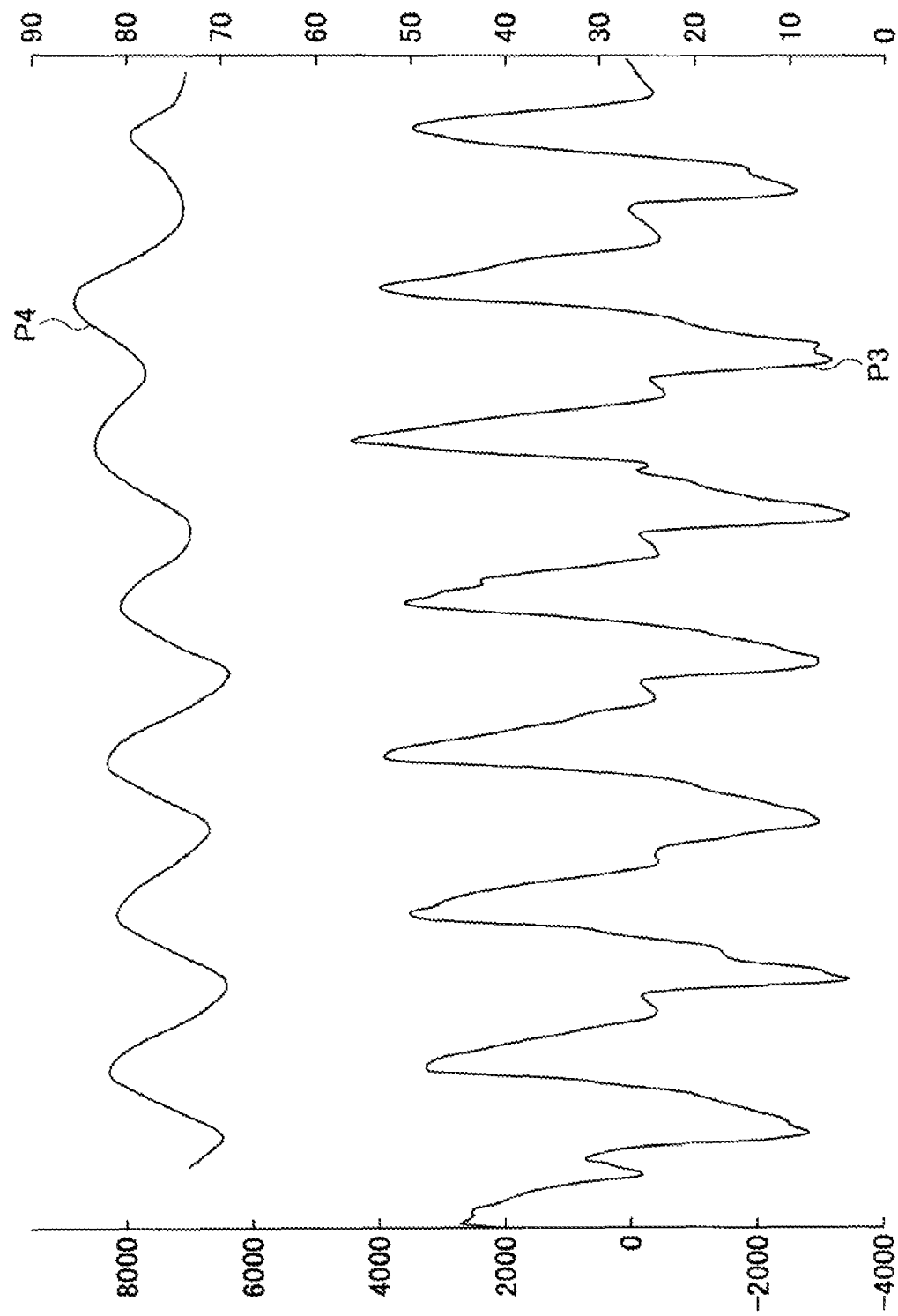
FIG. 6 is a diagram illustrating an example of time-series data of an RR interval and a respiration condition of a subject.

FIG. 6 shows an example of time-series data (waveforms) of the RR interval and a respiration condition of a subject. The respiration condition example of the subject is indicated by reference symbol P3. The time-series data of the RR interval (i.e., the change in the RR interval) is indicated by reference symbol P4. The RR interval may be calculated based on the detected R wave as described above. In some examples, the time-series data of FIG. 6 may be obtained concurrently with the time-series data of FIG. 5. The respiration condition may be measured with a thermistor attached to the tip of the nose of the subject. The thermistor may detect a temperature change accompanying breathing.

As shown in FIG. 6, the curve of the RR interval P4 may correlate with the curve of the respiration of the subject P3. Therefore, the respiration condition of the subject may be detected and a pause in breathing based on the RR interval derived from the detected R waves may be determined without attaching any device to the subject in a restraining way.

Figure 7A:
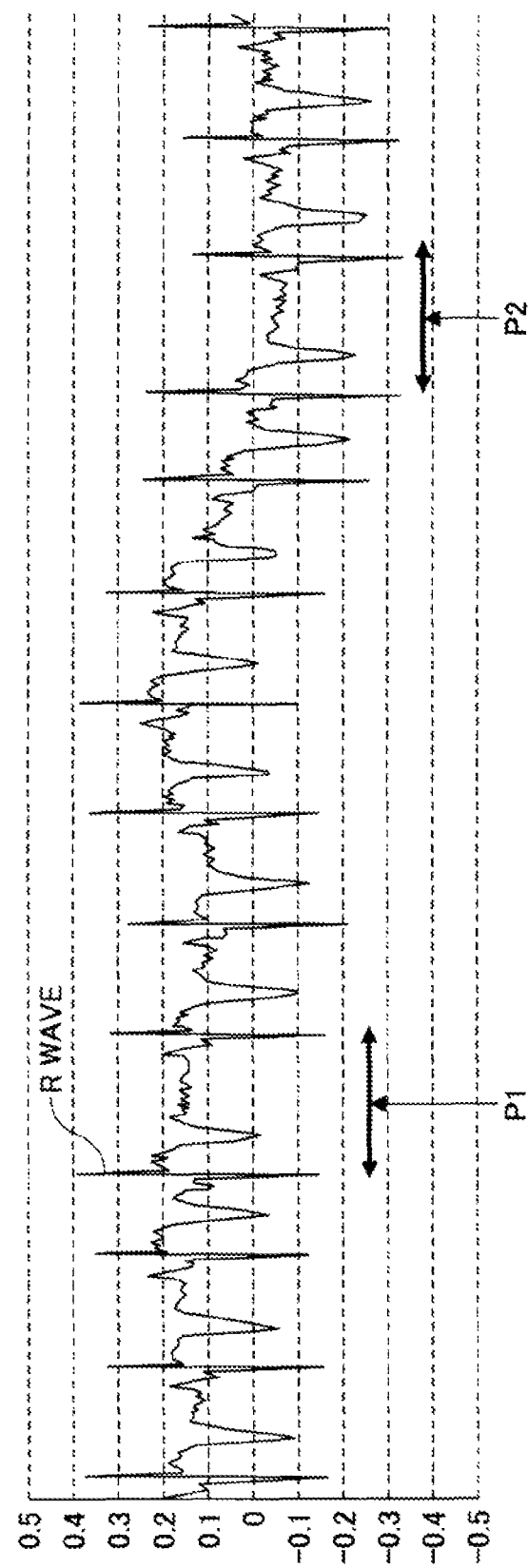
FIG. 7A is a graph of an example of time-series data of the RR interval in the case where there is normal breathing.
Figure 7B:
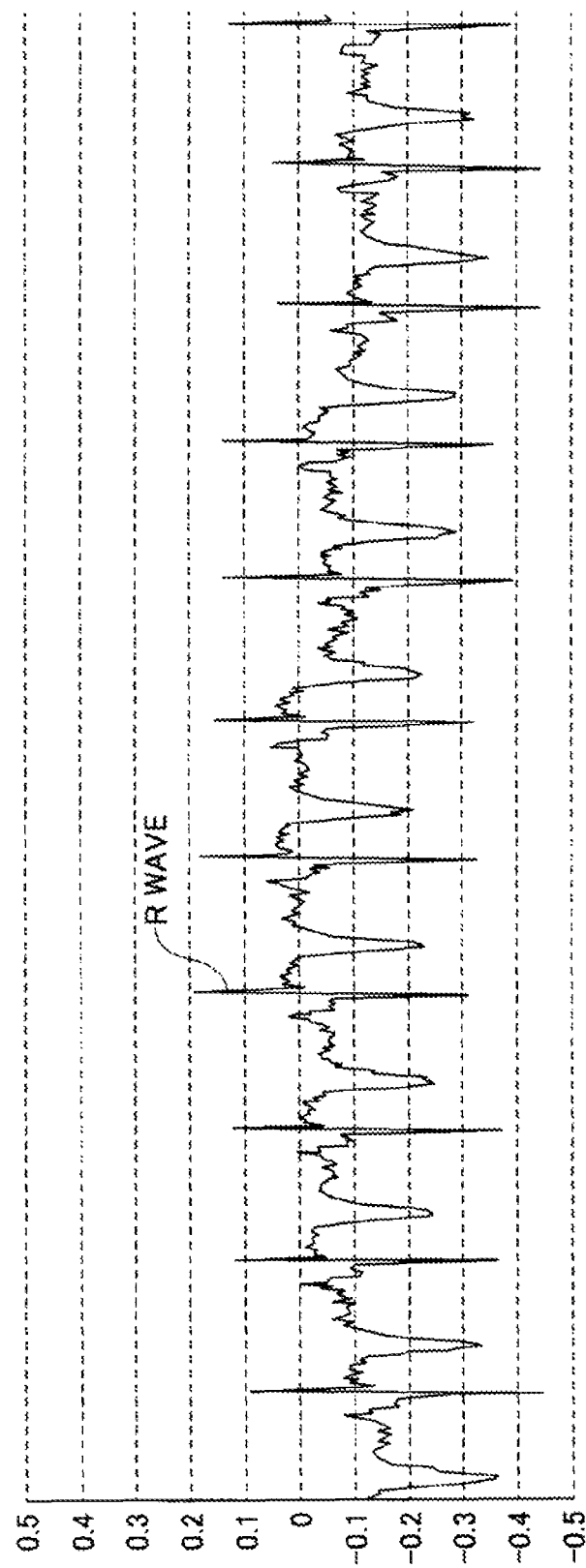
FIG. 7B is a graph of an example of time-series data of the RR interval in the case where there is a pause in breathing.

FIG. 7A is a graph of an example of time-series data of the RR interval in the case where there is normal breathing. FIG. 7B is a graph of an example of time-series data of the RR interval in the case where there is a pause in breathing. In FIG. 7A, a time period during which the subject breathes out may be indicated by P1 and P2. As shown in FIG. 7A, when the subject breathes out the RR interval may become longer. As shown in FIG. 7B, when the subject does not breathe out (i.e. there is a pause in breathing) the RR interval may not change substantially.

Therefore, in general, by utilizing this feature of the RR interval generated during a pause in breathing, it may be determined whether the calculated RR interval shows an abnormal tendency. For example, a pause in breathing may be detected based on an amplitude of a periodic change in the RR interval, a magnitude of the RR interval, or another characteristic of the RR interval.

In an example of the process shown in step 208 in FIG. 2, it may be determined that the calculated RR interval shows an abnormal tendency if an amplitude of a periodic change in the calculated RR interval in time series becomes less than a predetermined threshold for a predetermined time. In a normal state, the RR interval changes periodically in time series as shown in FIG. 5 and FIG. 7A. During the pause in breathing, the RR interval does not substantially change in time series, as shown in FIG. 7B. In other words, the amplitude of the waveform of the calculated RR interval may become smaller during the pause in breathing. This trend may be used to determine whether the calculated RR interval shows an abnormal tendency. In some examples, the predetermined threshold may be set to a fixed value between 70% and 90% of average amplitude of the RR interval. In other examples, the average amplitude may be set according to the characteristics of the subject, such as gender, age, etc. In some examples, the predetermined threshold may be adapted to match the subject individually. For example, the predetermined threshold may be set to a fixed value between 70% and 90% of average amplitude of the RR interval of the subject in question. The average amplitude may be set based on the actual measurement data obtained when the subject in question breathes normally during sleep. In some examples, the predetermined time period may be 10 seconds or longer. In an example, the predetermined time period may be around 30 seconds.

According to another example of the process in step 208 in FIG. 2, it may be determined that the calculated RR interval shows an abnormal tendency if the calculated RR interval does not exceed a predetermined interval in a predetermined time period. This algorithm may be based on the fact that the RR interval becomes longer than the predetermined interval when the subject breathes out as shown in FIG. 7A. The predetermined interval may be set based on experimental results or may be adapted to match with the subject, as described above. In some examples, the predetermined time period may be 10 seconds or longer, for example.

In such examples, a pause in breathing may be detected using the non-contact electrocardiograph 110 to measure the electrocardiogram.

Figure 8:
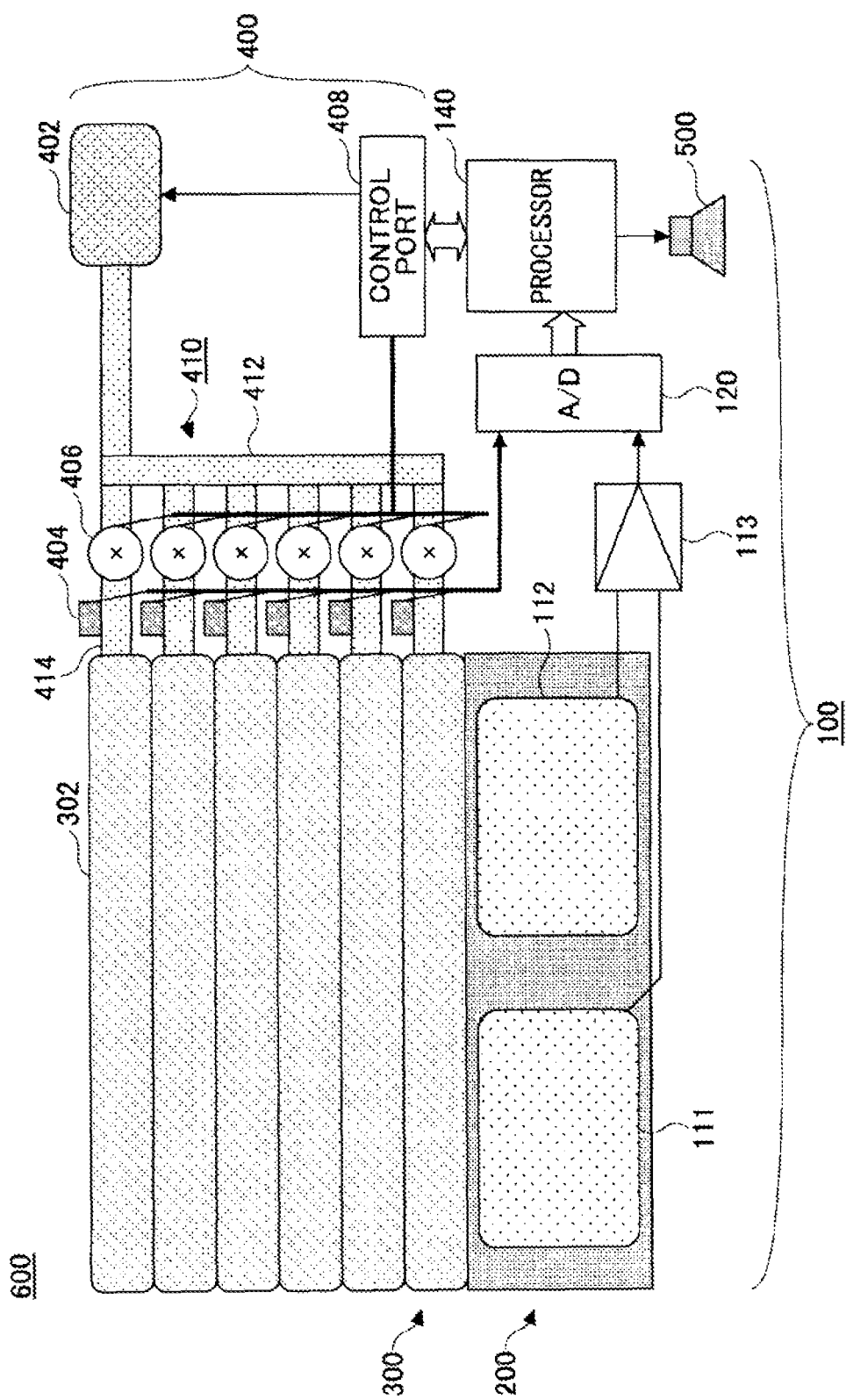
FIG. 8 is a diagram illustrating an embodiment of an emergency alert system 600.
Figure 9:
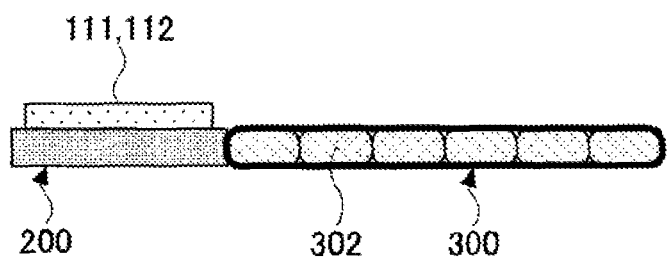
FIG. 9 shows a partial sectional view of FIG. 8.
Figure 10A:
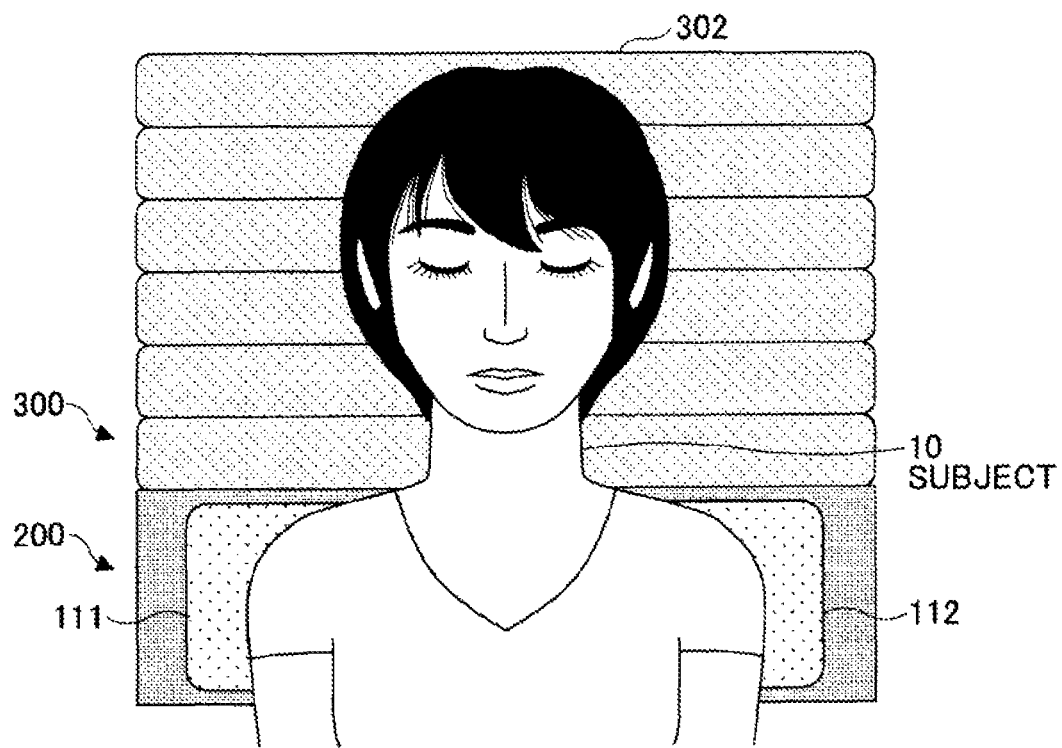
FIG. 10A is a plan view of a normal status of the subject lying down on a pad 200.
Figure 10B:
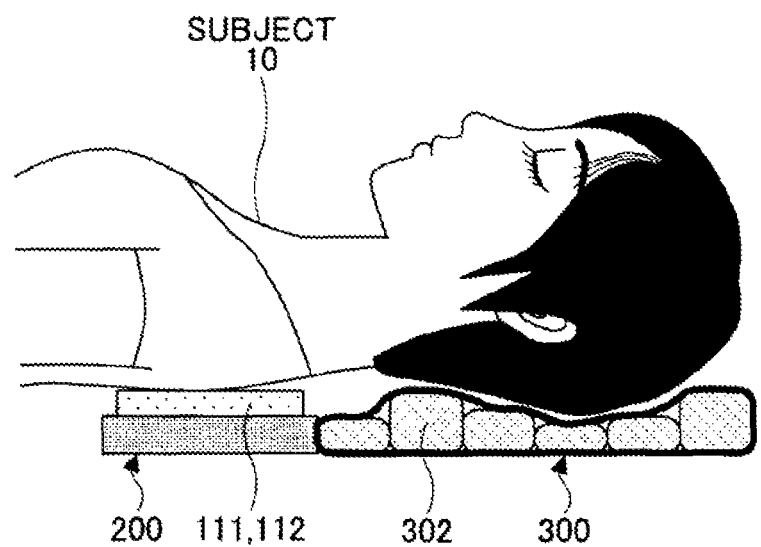
FIG. 10B is a sectional view of the pad 200 in a normal status of the subject lying down on the pad 200.

FIG. 8 shows an example of an emergency alert system 600. FIG. 9 shows a partial sectional view of FIG. 8. FIG. 10A and FIG. 10B show a normal status of the subject lying down on the pad 200.

In some examples, the emergency alert system 600 may be used for a patient who suffers from Sleep Apnea Syndrome (refereed to as SAS). In some examples, the system 600 may be used to diagnose SAS for any person, including a person who is not thought to suffer from SAS.

SAS may induce an apnea condition during sleep. The apnea may include a respiratory standstill of about 10 seconds or longer (i.e., a pause in breathing for 10 seconds or longer). A case in which an apnea condition during sleep is induced 5 times or more per hour or 30 times or more per 7 hours of sleep may be diagnosed as SAS. Some researches have reported that SAS may cause hypertension and cardiac disease. Even a mild case of SAS may induce microsleep, which may lead to a traffic accident or man-made calamity. Most SAS cases may be induced by the upper respiratory tract being obstructed by the pharynx. This type of SAS is called Obstructive SAS (OSAS).

The emergency alert system 600 may include the apparatus 100 described above, a pad 200, a pillow 300, an air supply system 400 and a speaker (or a buzzer) 500.

The electrodes 111, 112 of the apparatus 100 may be provided on the pad 200. The electrodes 111, 112 may be placed in areas on which respective left and right shoulders of the back of the subject may be positioned during sleep.

The pillow 300 may include a plurality of air tubes 302. The air tubes 302 may extend side by side in a transverse direction as shown in FIG. 8 and FIG. 9. The pillow 300 may be integrally formed with the pad 200 or it may be integrally incorporated in the pad 200.

The air supply system 400 may be configured to supply air to the respective air tubes 302 independently. In the illustrated example, the air supply system 400 includes a pump 402, pressure sensors 404, solenoid valves 406, a control port 408 and an air supply channel system 410.

The pressure sensors 404 may be installed to the pillow 300 to detect pressures in the air tubes 302. Electrical signals of the pressure sensors 404 may be supplied to the processor 140 via the analog-to-digital converter 120.

The air supply channel 410 may include a common channel 412 from which plurality of connecting channels 414 may be branched. Each connecting channel 414 may be connected to the corresponding air tube 302. Each connecting channel 414 may be provided with the corresponding solenoid valve 406 and the pressure sensor 404.

The processor 140 may be configured to control the respective solenoid valves 406 independently via the control port 408. The processor 140 may be configured to control the pump 402. The processor 140 may control the solenoid valves 406 and the pump 402 based on the output signals of the pressure sensors 404. For example, the processor 140 may control the solenoid valves 406 and the pump 402 to implement the respective target values of pressure in the respective air tubes 302.

In an example, the processor 140 may detect the subject on the pad when the RR interval is detected with the non-contact electrocardiograph 110, as described above. Simultaneously, the processor 140 may detect the subject on the pad based on the output signals of the pressure sensors 404. In a normal state, the solenoid valves 406 may be kept closed and air tubes 302 may be filled with air with at a predetermined pressure. In an example, the processor 140 may detect the subject on the pad if the pressure in the air tubes 302 increases.

Once the processor 140 detects the subject on the pad (see FIG. 10A), the processor 140 may initiate the process routine shown in FIG. 2, for example.

Figure 11:
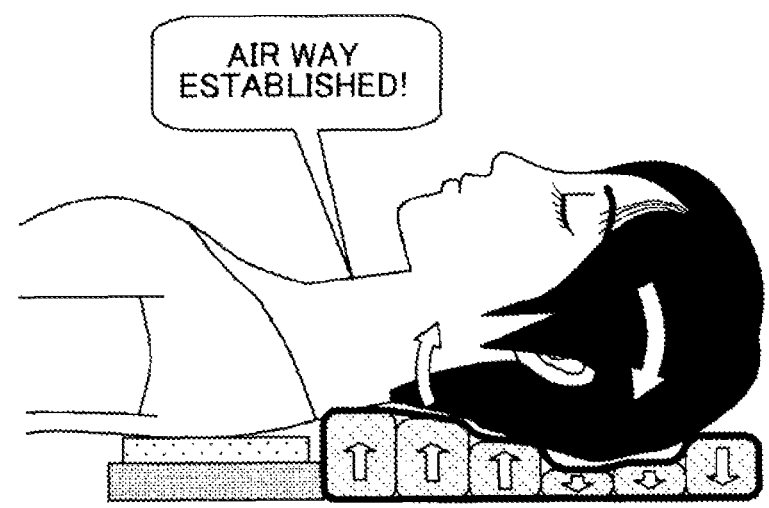
FIG. 11 is a diagram schematically showing an example of a way of deforming the shape of a pillow 300.

In an example of the process in step 210 shown in FIG. 2, when there is a pause in breathing of more than about 10 seconds, the processor 140 may determine an obstructive apnea condition. If a single obstructive apnea condition continues for about 30 seconds or more, the processor 140 may immediately operate under an emergency protocol. For example, the processor 140 may generate an alarm via the speaker 500. The alarm may be an alarm message or a sound which can awaken the subject. At the same time, the processor 140 may report the abnormality to others in the household or report the abnormality to a remote service, family members living separately, etc. via a communications interface. Further, if a brief apnea is detected at a specified frequency, the processor 140 may control the pressures in air tubes 302 in such a manner that an open airway may be established. Specifically, the processor 140 may identify the air tube 302 whose pressure is the highest and then take that position of the tube 302 with the highest pressure as the center of the head of the subject. Then, the processor 140 may estimate the position of the neck of the subject based on the estimated center of the head. Alternatively, the processor 140 may determine the position of the head and the neck of the subject from the distribution of the air pressure in the air tubes 302. Then, as schematically shown in FIG. 11, the processor 140 may establish an open airway by supplying air to the air tube(s) 302 positioned near the cervical region of the subject and exhausting air (i.e., reducing pressure) from the air tube(s) 302 positioned near the parietal region of the subject. In other words, the processor 140 may adjust the air pressure in the respective air tubes 302 to change the shape of the pillow 300 in such a manner that the chin of the subject is oriented upward so as to establish an open airway. In an example, the resumption of spontaneous breathing may be effected in the subject when an apnea condition is detected. In a normal state (i.e., where no abnormality is detected), the processor 140 may adjust the pressure in the respective air tubes 302 individually to keep the posture of the head of the subject suited for sound sleep.

According to the arrangement described above, it may be advantageous that the subject may not be required to wear additional devices on the body. This may avoid discomfort and allow the subject to sleep soundly. Further, it may be advantageous that the respiration condition of the subject may be monitored in an unrestrained way by using the non-contact electrocardiograph 110. Further, it may be advantageous that a pause in breathing may be detected using the non-contact electrocardiograph 110 to measure the electrocardiogram. Further, the position of the head may be detected via the pressure in the air tubes 302. Therefore, in some examples, the air pressure in the air tubes 302 may be controlled individually so that the pillow shape may be adjusted to keep the angle comfortable, resulting in sound sleep.

Figure 12:
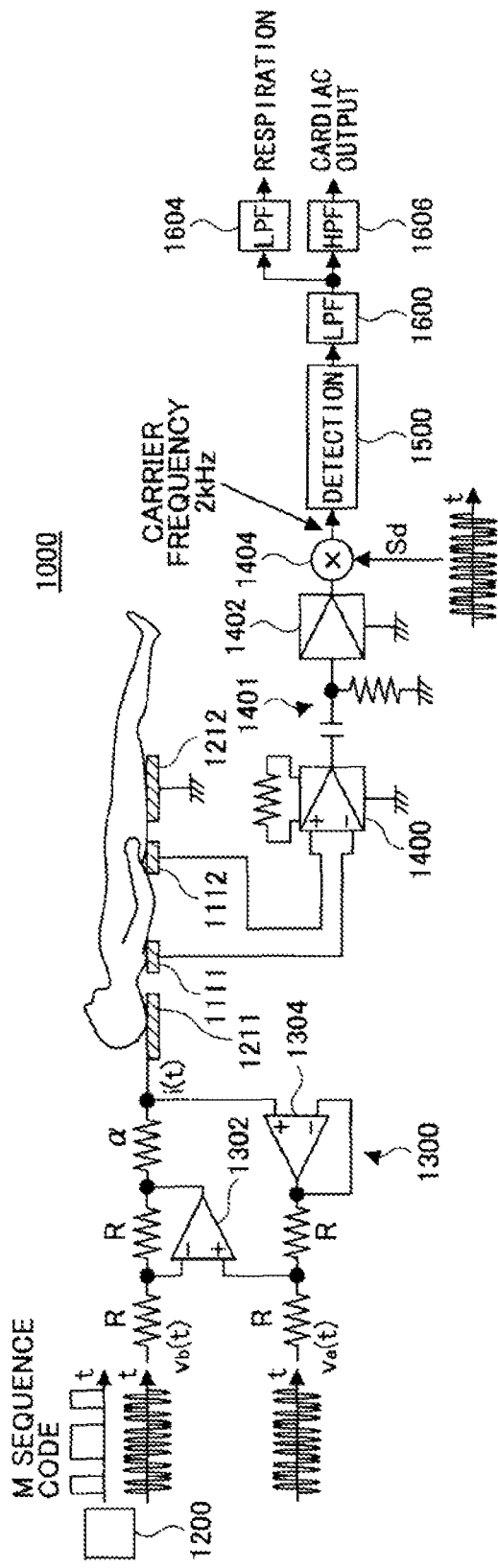
FIG. 12 is a diagram schematically showing another embodiment of an apparatus 1000 for detecting a respiration condition of a subject.

FIG. 12 shows an example of an apparatus 1000 for detecting a respiration condition of a subject.

The apparatus 1000 may include an m (maximal) sequence code generator 1200, a voltage-to-current converter 1300, a first pair of electrodes 1211, 1212, a second pair of detection electrodes 1111, 1112, a preamplifier (an instrumentation amplifier) 1400, a high-pass filter 1401, a head amplifier 1402, a mixer 1404, a detector circuit 1500, a low-pass filter 1600, a low-pass filter 1604 and a high-pass filter 1606.

Figure 13A:
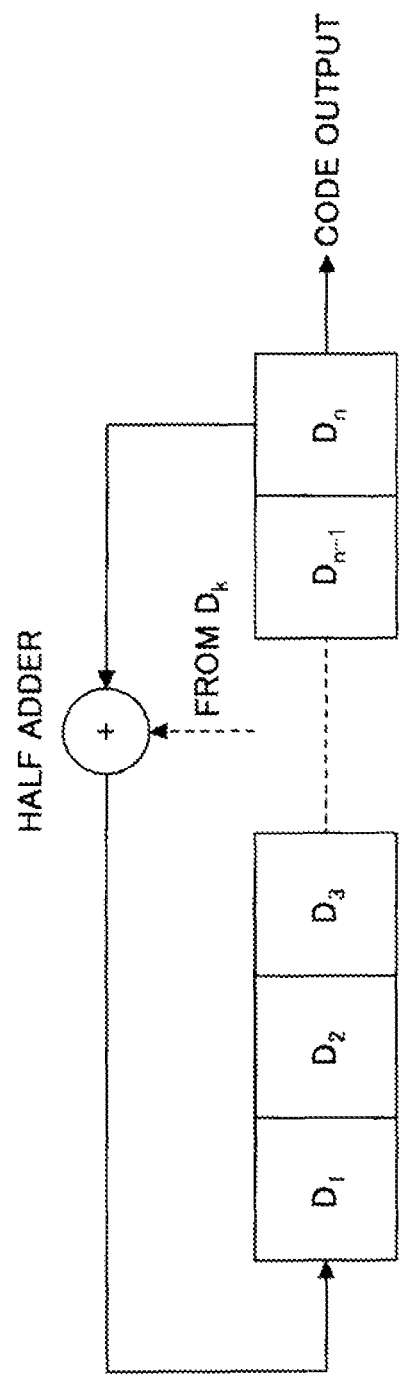
FIG. 13A is a diagram illustrating an example of an m sequence code generator.
Figure 13B:
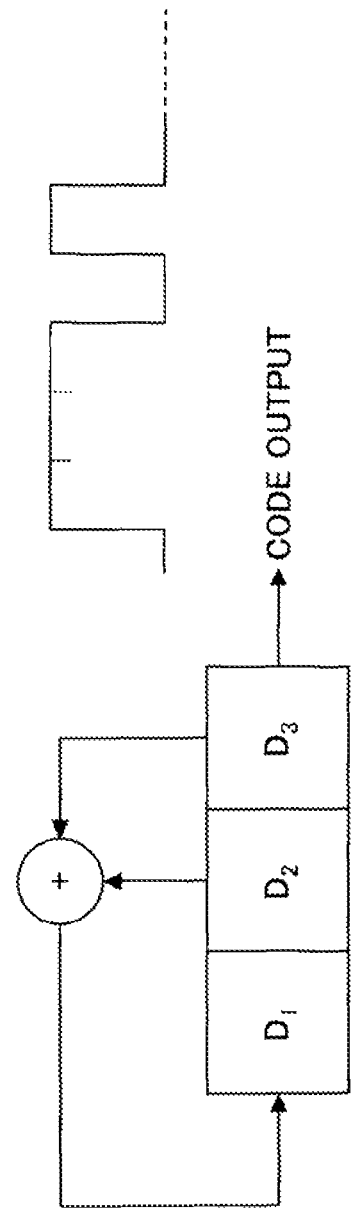
FIG. 13B is a diagram illustrating another example of a m sequence code generator.

The m sequence code generator 1200 may generate a wide-band m sequence code. The m sequence code may be a periodic bit sequence of binary code {1,−1}. The m sequence code generator may be configured using a shift register, a half adder, a clock generator, or other suitable circuitry. In various examples, the m sequence code generator may be configured as shown in FIG. 13A or FIG. 13B. In the example shown in FIG. 13A, the m sequence code with a 2N-1 bit cycle can be obtained from the n-stage shift register.

Figure 14:
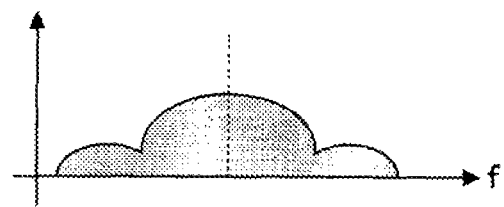
FIG. 14 is a diagram schematically showing a frequency spectrum of a current passing through the body of the subject.

The voltage-to-current converter 1300 may generate current i(t), which may be input to the electrode 1211, based on a differential input between the input voltages Vb(t) and Va(t). The input voltages Vb(t) and Va(t) may be generated by multiplying (i.e. phase-modulating) a carrier by the m sequence code generated by the in sequence code generator 1200. The voltages Vb(t) and Va(t) may be generated in such a manner that Vb(t) and Va(t) have opposite phases. The carrier frequency f0 may be between 50 kHz and 100 kHz. In an example, a frequency spectrum of the current i(t) may be spread over a wide range, as shown in FIG. 14. In other words, it may enable wide-band measurement of an electrical current signal (i.e., a change in impedance described below) obtained from the subject. Japanese Patent Application No. 2007-280739 discloses a noise diffusion restraint method using a code sequence such as an m sequence code, the entire contents of which are hereby incorporated by reference.

Shannon's Law of channel capacity may allow for increasing the obtained information when extracting biological information with a broadband signal. Specifically, according to Shannon's Law of channel capacity, the channel capacity C [bps] may be given by
Math $$C = W \cdot \log_2(1 + S/N)$$

where W [Hz] may be bandwidth, S [W] may be transmission power, and N [W] may be power of noise. From this formula, it can be seen that the channel capacity C can be increased if the bandwidth is widened.

Op-amplifiers (Operational amplifiers: ideal amplifiers) in the voltage-to-current converter 1300 may be the model AD823, which may be commercially available from Analog Devices. Inc.

The electrode 1211 may be provided in such a manner that it may be in indirect contact with the head of the subject, as shown in FIG. 12. The electrode 1212 may be provided in such a manner that it may be in indirect contact with a thigh of the subject, as schematically shown in FIG. 12. In some examples, the electrodes 1211 and 1212 may be provided in different manners. In an example, the electrode 1211 may be connected to a ground.

In the illustrated example, the current i(t) may pass through the body of the subject from the electrode 1211 to the electrode 1212.

The detection electrode 1111 may be in indirect contact with a first portion of the subject. The detection electrode 1112 may be in indirect contact with a second portion of the subject. The first and second portions may be selected such that the heart and the lungs of the subject may be located between the first and second portions. As shown in the illustrated example, the detection electrode 1111 may be provided in indirect contact with a shoulder of the back of the subject, and the detection electrode 1112 may be provided in indirect contact with the waist or the hips of the subject.

The impedance in the body of the subject between the detection electrodes 1111 and 1112 may change according to movements or activities of the heart and the lungs of the subject. In an example, the amount of blood in the heart may change according to the subject's heart beat and a cardiac output can be detected by monitoring the change in the impedance. In an example, the conductivity of the lung tissue may change according to the subject's respiration and the respiration can be detected by monitoring the change in the impedance.

The detection electrodes 1111 and 1112 may be connected to the preamplifier 1400. In an example, the amplification factor of the preamplifier 1400 may be selected to implement a hundredfold increase in power (output-to-input ratio of 100:1). The output of the preamplifier 1400 may be connected to the high-pass filter 1401. The high-pass filter 1401 may be implemented by a capacitor and a resistor, as shown in FIG. 12. The high-pass filter 1401 may be provided to extract desired alternating current components from the input current. The output of the high-pass filter 1401 may be connected to the head amplifier 1402. In an example, the amplification factor of the head amplifier 1402 may be selected to implement a hundredfold increase in power (output-to-input ratio of 100:1). The output of the head amplifier 1402 may be connected to the mixer 1404.

Here, the output signal of the head amplifier 1402 may be referred to as a detection signal. The detection signal may include information as to the cardiac output and the respiration of the subject (i.e. the change in impedance between the electrodes 1111 and 1112). In this example, as described above, since the current i(t) may be generated by modulating the carrier by the wide-band m sequence code, the detection signal can include such information as cardiac output, etc. in a wide band. Further, Johnson noise, 1/f noise, etc., which have no correlation with the modulated signal (i.e., the current i(t)), can be diffused over the wide band and thus reduced. In some examples, there may be a large amount of noise during non-contact measurement as the impedance may be high.

In the mixer 1404, the output of the head amplifier 1402 (i.e., the detection signal) and a signal Sd may be multiplied. The signal Sd may be generated by multiplying a carrier by the m sequence code generated by the m sequence code generator 1200. The carrier used to generate the signal Sd may have a carrier frequency f1 which may be different from the carrier frequency f0 used to generate the input current i(t). In an example, the carrier frequency f1 may be different from the carrier frequency f0 by about 2 kHz (i.e., f1=f0−2). In this way, the carrier frequency of the detection signal may be converted to a low frequency (i.e., 2 kHz in this example) so that digital signal processing may be implemented in a subsequent stage. Simultaneously, the m sequence demodulation may take place at the mixer 1404. The output of the mixer 1404 may be connected to the detector circuit 1500.

The detector circuit 1500 may detect (i.e., extract) a desired signal included in the output signal from the mixer 1404. The desired signal may correspond to a mixture of a cardiac output signal representing the cardiac output and a respiration signal representing the respiration of the subject. The output signal of the detector circuit 1500 may be passed though the low-pass filter 1600 to remove high frequency noise. The output signal of the low-pass filter 1600 may be passed though the low-pass filter 1604 and the high-pass filter 1606, respectively, to separate the respiration signal from the cardiac output signal.

The normal range of a heart rate may be between about 50 and 90 beats per a minute for a normal adult. A normal range of respiration rate may be between about 16 and 20 breaths per a minute. Thus, separation may be achieved between the respiration signal and the cardiac output signal by utilizing the difference in frequency. In an example, the low-pass filter 1604 and the high-pass filter 1606 may have a cutoff frequency of around 0.5 Hz.

Figure 15:
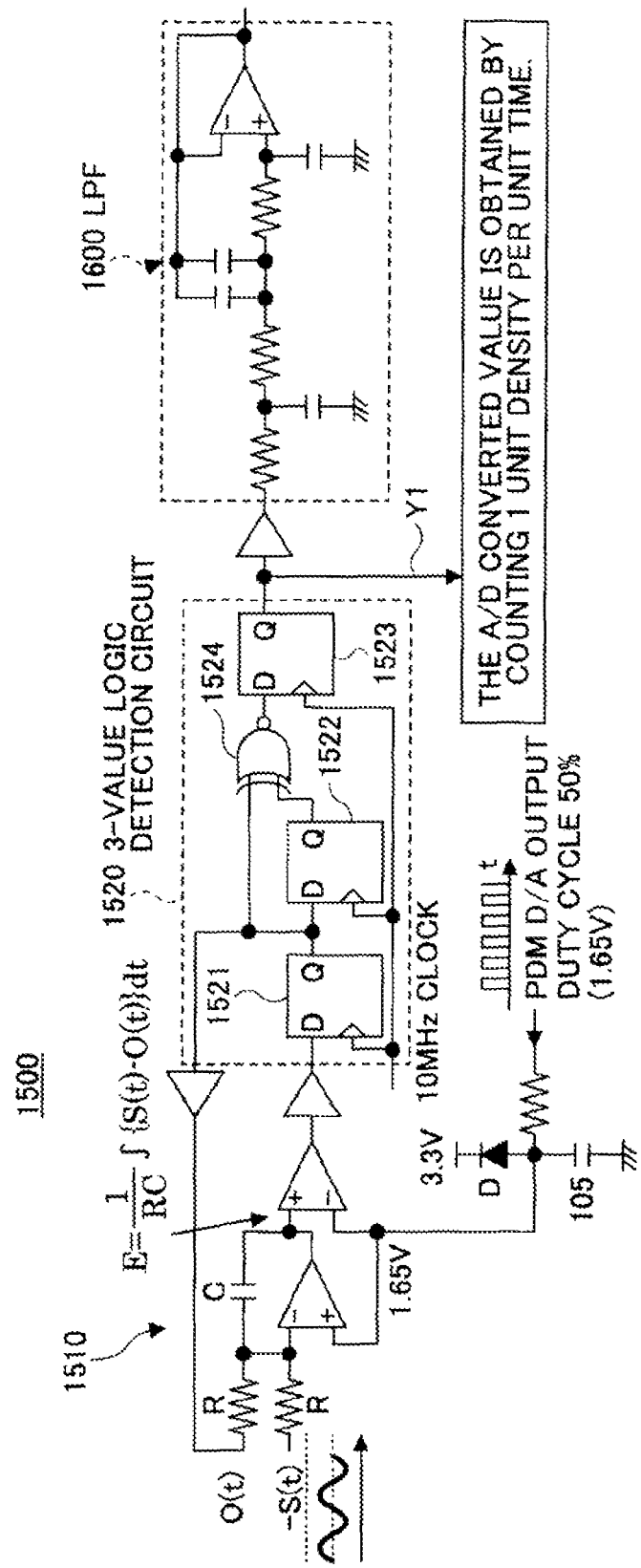
FIG. 15 is a diagram illustrating an example of a detector circuit 1500 and a low-pass filter 1600.

FIG. 15 shows an example of a detector circuit 1500 and a low-pass filter 1600 which may be used in the apparatus 1000.

As illustrated, in an example, the detector circuit 1500 may include a Delta Sigma A/D converter 1510 and a 3-value logic detection circuit 1520.

The Delta Sigma A/D converter 1510 may convert a differential between S(t) and O(t) into a digital form. The signal S(t) may correspond to the output signal of the mixer 1404. Op-amplifiers in the Delta Sigma A/D converter 1510 may be the model AD823, which may be commercially available from Analog Devices, Inc.

The 3-value logic detection circuit 1520 may include three D-type flip flops 1521, 1522 and 1523 and an Exclusive-NOR Gate 1524. A clock signal of 10 MHz may be input to the D-type flip flops 1521, 1522 and 1523. The output of the Delta Sigma A/D converter 1510 may be input to a D terminal of the D-type flip flop 1521. The output (Q) of the D-type flip flop 1521 may be connected to a D terminal of the D-type flip flop 1522. The output (Q) of the D-type flip flop 1521 may be connected to the input of the Delta Sigma A/D converter 1510 via a D/A converter to generate the signal O(t). The output (Q) of the D-type flip flop 1521 may be connected to an input of the Exclusive-NOR Gate 1524. The output (Q) of the D-type flip flop 1522 may be connected to another input of the Exclusive-NOR Gate 1524. FIG. 16 is a table for showing an example operation of the 3-value logic detection circuit 1520.

Figure 17:
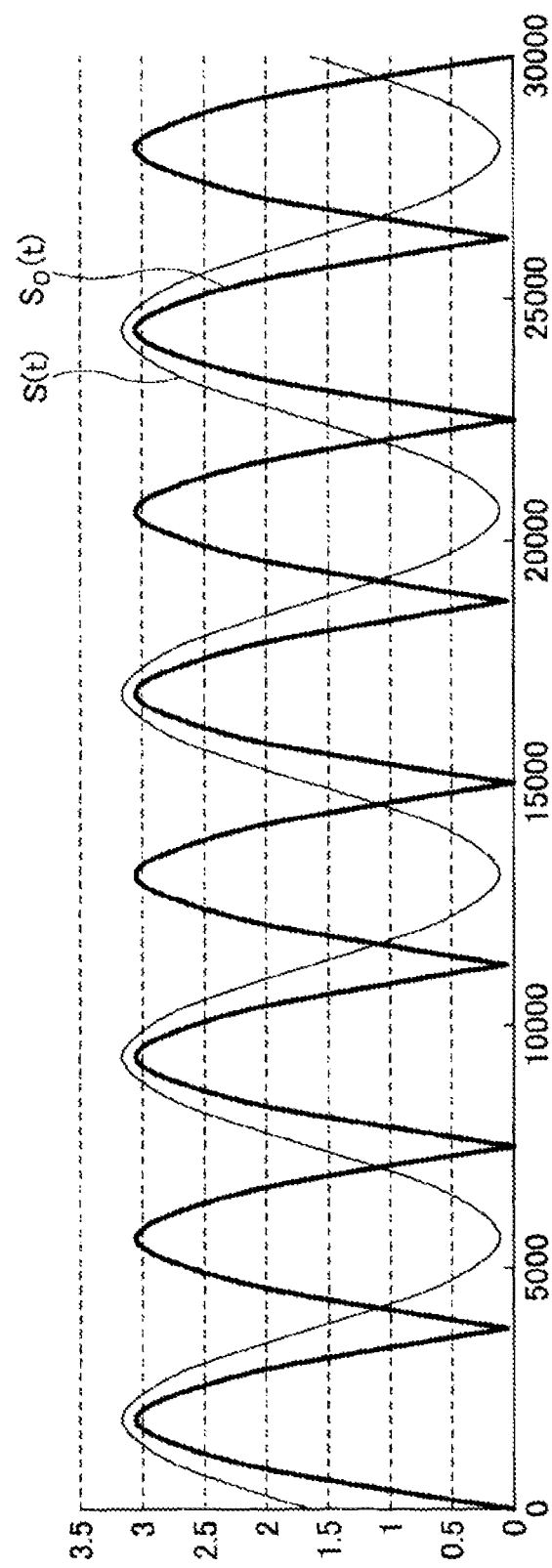
FIG. 17 is a diagram illustrating an example of a relationship between a signal S(t) and a signal SO(t).

The low-pass filter 1600 in the illustrated example may be implemented by using a positive feedback op-amplifier. From the low-pass filter 1600, the rectified value SO(t) may be obtained with a cut-off frequency. FIG. 17 shows an example of a relationship between the signal S(t) and the signal SO(t).

The A/D converted value may be obtained by counting 1 unit of density per unit time, as indicated by arrow Y1 in FIG. 15. In this example, the low-pass filter 1600 may be omitted.

According to the disclosure related the example disclosed above, non-invasive impedance plethysmography using a noise diffusion restraint method (a Spread Spectrum Communication System applied to the measuring method) may be implemented. This method may use the autocorrelation property of the m sequence code and may be highly sensitive, noise-resistant, independent of the subject's sleeping position and posture, and capable of non-invasive biological information monitoring. This monitoring method can be utilized in non-invasive biological information measurement in, for example, a bathroom or a shower room, and can also be used for measuring salinity (blood monitoring).

In various examples, the apparatus 1000 may be used in the emergency alert system 600 instead of the apparatus 100.

It should be understood that variations and modifications may be made without departing from the disclosure.

For example, in an above described example, the electrocardiogram may be processed to detect a pause in breathing in real time: however, the electrocardiogram may be processed in non-real time.

Further, in an above described example, air may be used to deform the pillow 300: however, other fluids such as, for example, water may be used instead of air.

Further, in an above described example, the m sequence code may be used to implement wide-band measurement: however, other code sequences which may have high orthogonality between codes, a pseudo-random property, high autocorrelation and periodicity may also be used.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs). Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc., and a transmission type medium such as a digital and/or an analog communication medium (e.g., a fiber optic cable, a waveguide, a wired communication link, a wireless communication link, etc.).

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to." the term "having" should be interpreted as "having at least." the term "includes" should be interpreted as "includes but is not limited to." etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g. the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g. "a system having at least one of A, B, and C" would include but not be limited to systems that have A alone, B alone, C alone, A and B together, A and C together. B and C together, and/or A, B, and C together, etc.). In those instances where a convention analogous to "at least one of A, B, or C, etc." is used, in general such a construction is intended in the sense one having skill in the art would understand the convention (e.g. "a system having at least one of A, B, or C" would include but not be limited to systems that have A alone. B alone, C alone, A and B together, A and C together. B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. A method of detecting an apnea condition in real time, comprising:
    obtaining an electrocardiogram using a non-contact electrocardiograph including two electrodes and an amplifier, the two electrodes being provided on a pad and configured to be in indirect contact with left and right shoulders of a subject in contact with the pad, the amplifier being capable of operating on femtoampere (fA)-class input bias current;
    detecting rectangular (R) waves in the electrocardiogram by calculating a cross-correlation between the electrocardiogram and a rectangular-wave time window, the rectangular-wave time window including a first negative pulse, a positive pulse and a second negative pulse, wherein the ratio of widths of the first negative pulse, the positive pulse and the second negative pulse is about 1:2:1;
    calculating an R wave to R wave (RR) interval in the electrocardiogram based on the detected R waves, wherein the RR interval is a time interval between two consecutive R waves,
    determining whether an amplitude of a periodic change in calculated RR intervals in time series is less than a predetermined threshold, and
    detecting the apnea condition if the amplitude of the periodic change is less than the predetermined threshold for about 10 seconds,
    wherein the detecting the apnea condition is performed in real time during sleep; the method further comprising:
    providing a pillow which includes tubes that support a head of the subject, the tubes having fluid supplied therein, and
    adjusting an amount of fluid in the tubes that support the head of the subject, if a pause in breathing longer than a predetermined time is detected.

2. The method as claimed in claim 1, wherein the tubes extend in a transverse direction side-by-side, and the adjustment of the amount of the fluid in the tubes includes supplying the fluid to a first tube of the tubes, the first tube being positioned near a cervical region of the subject and reducing a fluid pressure in a second tube of the tubes, the second tube being positioned near a parietal region of the subject.

* * * * *

UNITED STATES PATENT AND TRADEMARK OFFICE
CERTIFICATE OF CORRECTION

PATENT NO. : 8,483,811 B2
APPLICATION NO. : 13/000127
DATED : July 9, 2013
INVENTOR(S) : Ueda It is certified that error appears in the above-identified patent and that said Letters Patent is hereby corrected as shown below:

On Title Page 2, in Item (56), under "OTHER PUBLICATIONS", in Column 1, Line 2, delete "Jiang" and insert -- (Jiang --, therefor.

On Title Page 2, in Item (56), under "OTHER PUBLICATIONS", in Column 2, Line 2, delete "Climical" and insert -- Clinical --, therefor.

In the Specification

In Column 1, Line 44, delete "window:" and insert -- window; --, therefor.

In Column 1, Line 49, delete "cross-correlation:" and insert -- cross-correlation; --, therefor.

In Column 1, Line 51, delete "subject:" and insert -- subject; --, therefor.

In Column 2, Line 4, delete "generator:" and insert -- generator; --, therefor.

In Column 2, Line 10, delete "1520:" and insert -- 1520; --, therefor.

In Column 4, Line 11, delete "D0-D 5" and insert -- D0-D15 --, therefor.

In Column 5, Line 15, delete "(i.e." and insert -- (i.e., --, therefor.

In Column 6, Line 7, delete "(refereed" and insert -- (referred --, therefor.

In Column 7, Line 15, delete "etc." and insert -- etc., --, therefor.

In Column 8, Line 10, delete "(i.e." and insert -- (i.e., --, therefor.

Signed and Sealed this
Eighth Day of April, 2014

Michelle K. Lee
*Deputy Director of the United States Patent and Trademark Office*

CERTIFICATE OF CORRECTION (continued)
U.S. Pat. No. 8,483,811 B2

In Column 8, Line 11, delete "the in" and insert -- the m --, therefor.

In Column 9, Line 22, delete "(i.e." and insert -- (i.e., --, therefor.

In Column 9, Line 26, delete "etc." and insert -- etc., --, therefor.

In Column 9, Line 41, delete "way," and insert -- way; --, therefor.

In Column 12, Line 28, delete "not limited to."" and insert -- not limited to," --, therefor.

In Column 12, Line 30, delete "not limited to."" and insert -- not limited to," --, therefor.

In Column 12, Line 51, delete "(e.g." and insert -- (e.g., --, therefor.

In Column 12, Line 57, delete "(e.g." and insert -- (e.g., --, therefor.

In Column 12, Line 64, delete "(e.g." and insert -- (e.g., --, therefor.